(12) United States Patent  (10) Patent No.: US 8,272,603 B2
Fadler et al.  (45) Date of Patent: Sep. 25, 2012

(54) IMAGING SYSTEM STAND

(75) Inventors: Franz Fadler, Hetzles (DE); Paul Weidner, Pressath (DE); Satchi Panda, Fremont, CA (US)

(73) Assignee: Siemens Aktiengesellschaft, Munich (DE)

( * ) Notice: Subject to any disclaimer, the term of this patent is extended or adjusted under 35 U.S.C. 154(b) by 371 days.

(21) Appl. No.: 12/625,172

(22) Filed: Nov. 24, 2009

(65) Prior Publication Data

US 2010/0163694 A1    Jul. 1, 2010

(30) Foreign Application Priority Data

Nov. 27, 2008  (DE) .......................... 10 2008 059 331

(51) Int. Cl.
*F16M 11/00*  (2006.01)
(52) U.S. Cl. ................. 248/123.2; 248/125.1
(58) Field of Classification Search ............. 248/123.11, 248/122.1, 123.2, 125.1, 125.2, 132, 162.1, 248/410, 331; 192/30 R
See application file for complete search history.

(56) References Cited

U.S. PATENT DOCUMENTS

| | | | | |
|---|---|---|---|---|
| 4,158,490 A | * | 6/1979 | Gottschalk et al. | 352/243 |
| 4,334,155 A | * | 6/1982 | Gieschen et al. | 378/196 |
| 4,344,595 A | * | 8/1982 | Heller et al. | 248/542 |
| 4,544,121 A | | 10/1985 | Komura | |
| 6,119,605 A | * | 9/2000 | Agee | 108/147 |
| 6,471,165 B2 | * | 10/2002 | Twisselmann | 248/123.11 |
| 6,592,086 B1 | * | 7/2003 | Sander | 248/123.11 |
| 8,038,108 B2 | * | 10/2011 | Yasunaga et al. | 248/123.2 |
| 2002/0064048 A1 | * | 5/2002 | Sander | 362/401 |
| 2003/0230698 A1 | * | 12/2003 | Strauss et al. | 248/648 |
| 2009/0097840 A1 | * | 4/2009 | Amadril et al. | 396/428 |
| 2010/0006717 A1 | * | 1/2010 | Weber et al. | 248/125.2 |
| 2011/0297800 A1 | * | 12/2011 | Metelski | 248/123.2 |

FOREIGN PATENT DOCUMENTS

DE  102005031494 A1  1/2007

OTHER PUBLICATIONS

German Office Action dated May 14, 2009 with English translation.

* cited by examiner

*Primary Examiner* — Ramon Ramirez
(74) *Attorney, Agent, or Firm* — Lempia Summerfield Katz LLC

(57) ABSTRACT

A stand, in particular a floor stand, having an arm for holding an object, in particular an imaging device in the form of an ultrasound transducer, said arm being mounted on a vertical column and movable vertically via a vertical guide, wherein a counterweight balancing the weight of the arm is provided on or in the vertical column, a device (24) being provided for moving the counterweight (21) counter to the weight force ($F_G$) for at least partially overriding the counterbalance.

18 Claims, 5 Drawing Sheets

IMAGING SYSTEM STAND

The present patent document claims the benefit of DE 10 2008 059 331.1 filed Nov. 27, 2008, which is hereby incorporated by reference.

BACKGROUND

The present embodiments relate to a stand having an arm for holding an object.

Stands are frequently used with medical imaging devices, such as ultrasound transducers, and have an arm. The arm is coupled to a vertical column in a vertically movable manner. An imaging device, such as an ultrasound transducer is disposed on the arm. Maneuverability of the ultrasound transducer is provided via the maneuverability of the arm and by ball joint mounting the imaging device on the arm. The imaging device may be an ultrasound transducer or a larger device or module, for example having a frame or the like. The imaging device is applied to the patient and positioned by a doctor, for example, to image a breast in the case of a mammogram. The doctor orients the ultrasound transducer according to the position of the breast in order to correctly position the ultrasound transducer relative to the breast or a specific point (e.g., the nipple) and be able to capture the images showing the entire region of interest, from which three-dimensional (3D) images are subsequently reconstructed. Because of the maneuverability of the arm and the ball joint mounting of the imaging device, the ultrasound transducer may be placed in any position depending on the location and/or size of the breast.

During a mammogram, the ultrasound transducer is applied with considerable pressure, and this pressure is maintained during scanning, for example, by pressing on the breast. When using an ultrasound imaging device incorporating a stand, the patient is lying down so that the doctor can apply the ultrasound transducer from above or displaced slightly to the side and press the ultrasound transducer on the patient. The ultrasound transducer is pressed with high compressive force against the breast throughout the image capture process.

The user (e.g., the doctor) is required to press the imaging device in position with high expenditure of effort for the entire duration of scanning, which may last one or more minutes until all the images enabling 3D reconstruction have been obtained. This is tiring for the user. Accordingly, the doctor may be unable to maintain the pressure for the entire time, resulting in a change in the position of the ultrasound transducer, may shake while applying the pressure, or a position change may occur due to respiratory movement in conjunction with manual application of pressure. The position change has a negative effect on the quality of the images obtained.

SUMMARY AND DESCRIPTION

The present embodiments may obviate one or more of the drawbacks or limitations in the related art. For example, in one embodiment, a stand may improve image capture.

In one embodiment, a stand may include a device for varying a counterbalance, such that a resulting weight force acting in the direction of a weight force of an arm occurs.

In one embodiment, the counterbalance is provided via a counterweight and enables a user to move a counterbalanced arm effortlessly in space. The counterbalance may be partially overridden temporarily (e.g., for the duration of scanning) when an imaging device must be firmly pressed onto an examination subject, so that the arm automatically presses with at least part of the weight of the arm onto the examination subject (e.g., in the case of mammography, a breast). The user is unburdened and does not press unaided, as in the prior art, on the imaging device with much expenditure of effort. Rather, the counterbalance may be partially overridden so that the stand operates in a quasi "self-acting" manner, and the imaging device is pressed on using the weight of the imaging device or more precisely, a resulting weight force of the arm. The device may move the counterweight automatically against the weight force. Accordingly, the device "lifts" the counterweight so that the weight of the arm, counter-supported via the imaging device already resting on the examination subject, is no longer completely balanced (e.g., the weight of the arm presses the imaging device on the patient using the resulting difference in weight, the difference between the weight of the arm and the "reduced" counterweight). As the arm, in conjunction with the imaging device, has a considerable total weight, a sufficiently high pressing-on force can be generated within the stand, depending on the extent to which the counterbalance is overridden. Accordingly, the user is unburdened, and the pressing-on force remains constant throughout the scanning process. As a result, no appreciable position changes due to unintentional relaxation occur during image capture, because the resulting pressure-exerting weight remains unchanged during the scanning time.

The device may move the counterweight against the weight force of the device in order to vary an obtained equilibrium of forces.

The device may engage with an axis of rotation of a traction roller via which a traction device (e.g., a cable, a belt or a chain), connecting the arm to the counterweight, runs. The device is therefore indirectly coupled to the counterweight via the axis of rotation of the traction roller. The counterweight may be "lifted" by suitable application of torque via the device to the axis of rotation of the traction roller, as the traction device is in turn moved and, via the traction device, the counterweight is "lifted" against the weight force of the arm. It is not necessary to "lift" the counterweight over a particular path length; rather, for varying the counterbalance, a force that cooperates with the weight force of the arm and is introduced into the traction system via the axis of rotation of the traction roller suffices.

The device may include a servomotor for driving the axis of rotation of the traction roller, and a clutch, via which the servomotor may be operatively connected to the axis of rotation. The servomotor, which may be disengaged (e.g., not operatively connected to the axis of rotation), may be coupled to the axis of rotation of the traction roller, via the clutch, to override the counterbalance and press the arm onto the examination subject.

In one embodiment, a first pinion may be driven via the servomotor and meshes with a second pinion, which may be brought into rotary connection with the axis of rotation of the traction roller via the clutch. A pinion combination is therefore provided and includes a first pinion, which is driven via the servomotor (e.g., by a gear downstream of the servomotor) and meshes with a second pinion. The second pinion lies on the axis of rotation of the traction roller, but as long as the clutch is open, the second pinion is not motionally coupled to the axis of rotation of the traction roller and idles. Only when the clutch closes is the second pinion drive-coupled to the axis of rotation of the traction roller with resulting force transmission or, more specifically, transmission of the torque produced via the servomotor to the axis of rotation of the traction roller.

In one embodiment, the clutch is a friction clutch, which provides a sufficient degree of safety in that the counterbalancing is not excessively or completely overridden, and the arm is not pressed onto the examination subject with excessively high residual force or the entire weight of the arm. The friction clutch may be configured so as to define a maximum torque that can be transmitted from the servomotor via the clutch. If the maximum torque is reached, the clutch will slip so that no further torque transmission, and therefore, no excessively heavy loading of the axis of rotation of the traction roller, becomes possible (e.g., no excessive release to produce an excessively heavy pressure).

The friction clutch may slip, both in the case of excessive loading via the servomotor and in the case of excessive loading of the axis of rotation of the traction roller via the arm (e.g., the friction clutch may slip in both directions). If the counterbalance is partially overridden via the device, and the examination subject feels the increasing weight of the arm, fear or anxiety may arise, resulting in the examination subject attempting to push the arm up. The arm may be pushed up for reasons of patient safety (e.g., the clutch allows this counter movement). The friction clutch may be configured to slip in both directions to both prevent excessive loading on the part of the servomotor and to allow the patient to actively press against the arm and reduce the pressure.

Even though the clutch (e.g., the friction clutch) may be of many different designs, in one embodiment, the clutch is a solenoid operated clutch, which opens or closes the operative connection when corresponding magnetic fields are generated (e.g., when a current flows), or no longer generated. Such solenoid operated clutches switch very rapidly and may be very precisely set, via which the desired maximum torques, whether it be on the part of the servomotor or on the part of the arm being pushed up, may be precisely set.

In one embodiment, the device (e.g., the servomotor and the solenoid operated clutch) may be controlled via at least one actuating element (e.g., a pushbutton) on the arm or on the imaging device. The imaging device is manually applied and positioned by the user. In order to actuate the imaging device and generate the contact pressure, the user may actuate the actuating element on the arm or on the imaging device without taking his or her hands off. The user does not need to change his or her grip, which might ultimately result in a re-positioning. For this purpose, the actuating element may be located in an area on the imaging device, on which the user has his or her hands so that the user may press the pushbutton or the like with one finger.

In one embodiment, an actuating element (e.g. a pushbutton), may be pressed a first time to move the counterweight and a second time for re-counterbalancing (e.g., if the patient is to have the pressure released again). In one embodiment, the actuating element may include a joystick, which may be moved in one direction to move the counterweight, or another for re-counterbalancing. One embodiment may include separate actuating elements (e.g., two separate pushbuttons), a first actuating element being used for partial overriding of the counterbalance and a second actuating element being used for control for re-setting the counterbalance.

DETAILED DESCRIPTION

Figure 1:
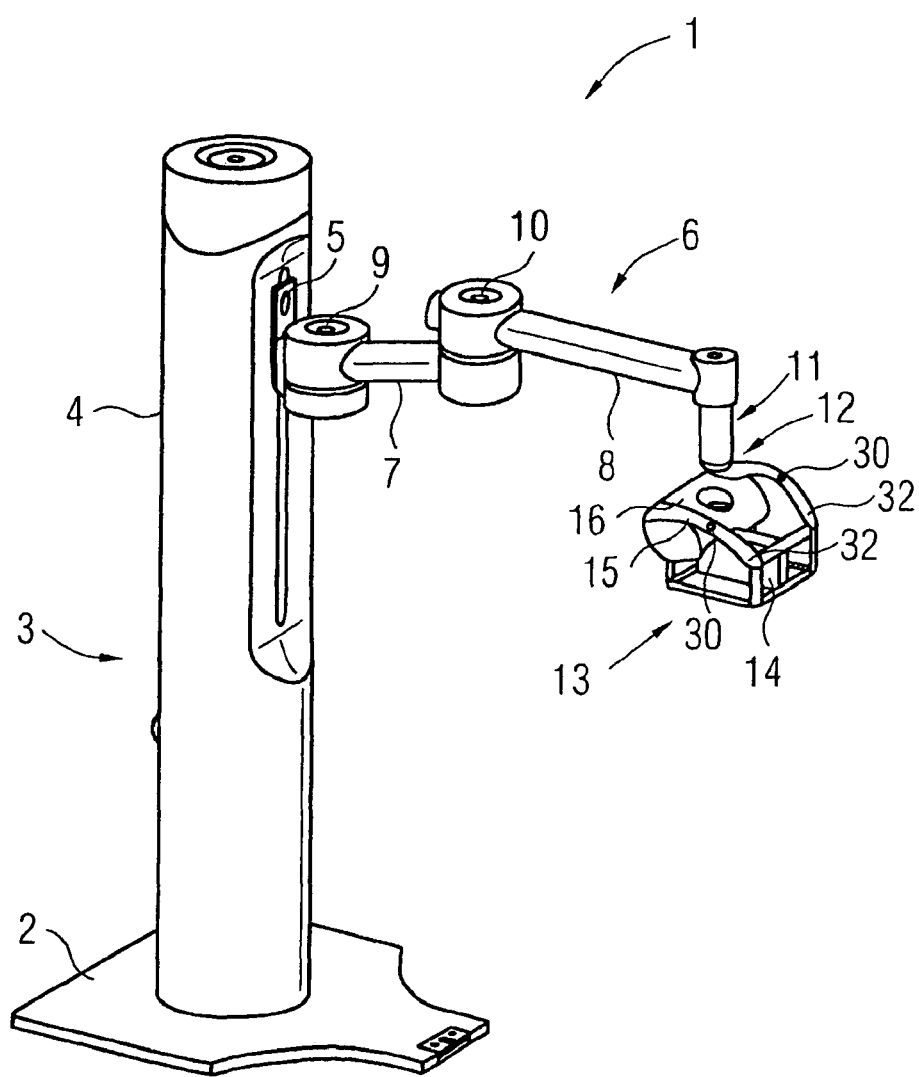
FIG. 1 shows one embodiment of a stand.
Figure 2:
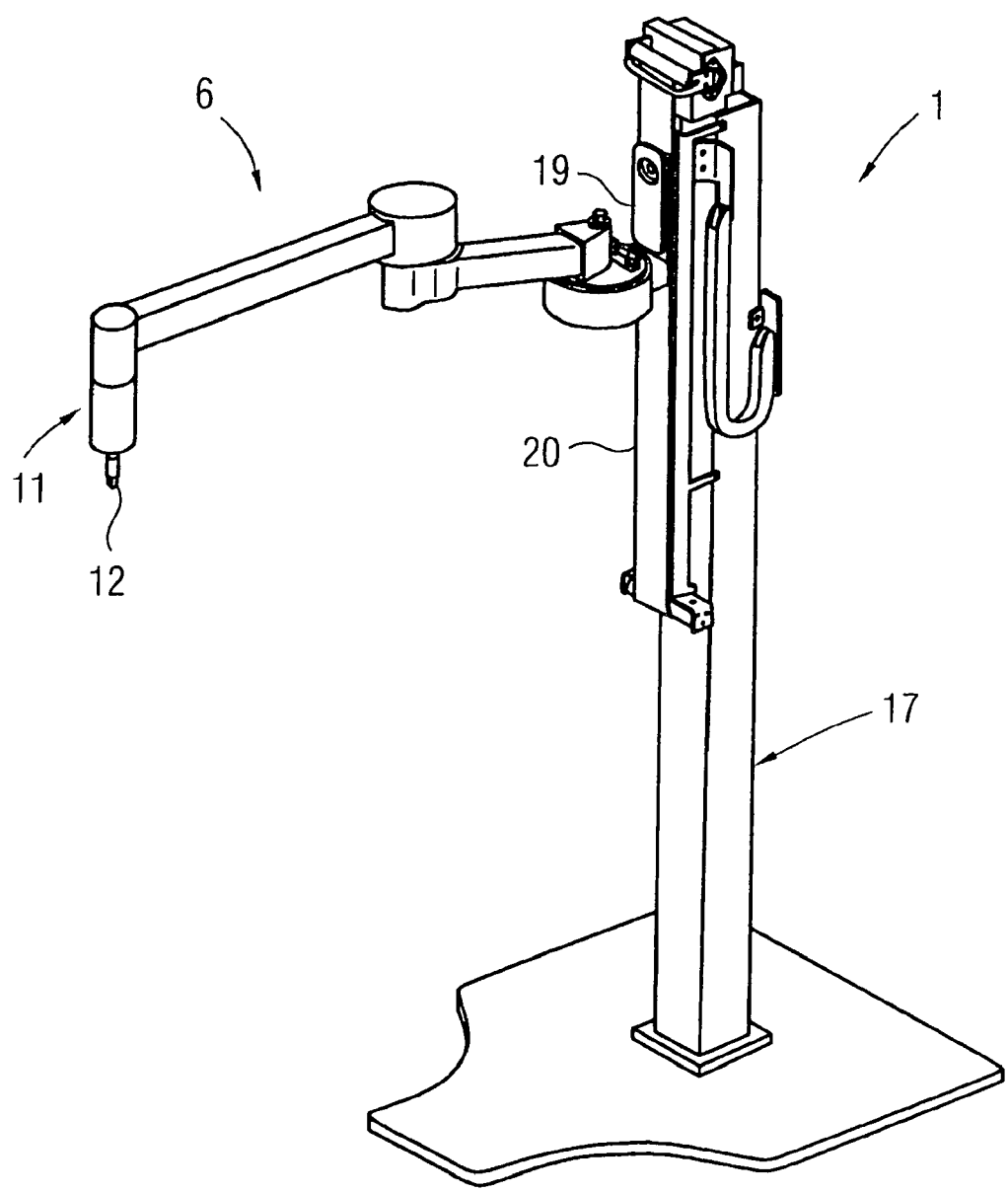
FIG. 2 shows one embodiment of the stand from FIG. 1 with the paneling removed.

FIG. 1 shows a stand 1, such as a floor stand, with a base plate 2. A vertical column 3 with paneling 4 is disposed on the base plate 2. Guided vertically on the vertical column 3 is an arm 6 that includes two arm sections 7, 8 and is vertically movable via a linear guide 5. The arm 6 may be swiveled relative to the linear guide 5 via a first pivot joint 9, and a second pivot joint 10 located between the arm sections 7 and 8. The second pivot joint 10 also enables the two arm sections 7 and 8 to swivel relative to one another. On an end of the arm section 8 is an adapter 11 on which an attachment section 12, as shown in FIG. 2, is provided. An imaging device 13 (e.g., an ultrasound transducer 14 for capturing ultrasound images in the context of a mammogram), may be detachably mounted to the attachment section 12. The imaging device 13 may have a frame-like housing 15, on which a section 16 is provided with various operating devices (e.g., a swivel motor, a control device), as well as the ultrasound transducer 14, which may be pivotably movable. The imaging device 13 may be mounted to the attachment section 12 of the arm 6 via a mounting section, where the imaging device 13 may be rotated and swiveled in order to enable the imaging device 13 to be oriented precisely with respect the breast for which the mammogram is to be taken. The orientation may be carried out such that the ultrasound transducer is oriented relative to a fixed point on the breast (e.g., the nipple), so that the ultrasound transducer is above the fixed point on the breast. For scanning, the ultrasound transducer is then moved via an imaging device movement device from the fixed point on the breast to the respective sides in order to ultrasonically scan the breast.

FIG. 2 shows the stand 1 without the paneling 4 enclosing the vertical column 3 and the arm 6, exposing a vertical support 17. The vertical column includes the vertical support 17, on which a vertical guide rail 18 (see FIG. 3) is provided. A guide carriage 19 runs on the vertical guide rail 18 and couples the arm 6 with the vertical support 17. In FIG. 2, the vertical guide rail 18 is concealed by a curtain plate 20. The basic construction of a vertical guide of this kind is sufficiently well known.

Figure 3:
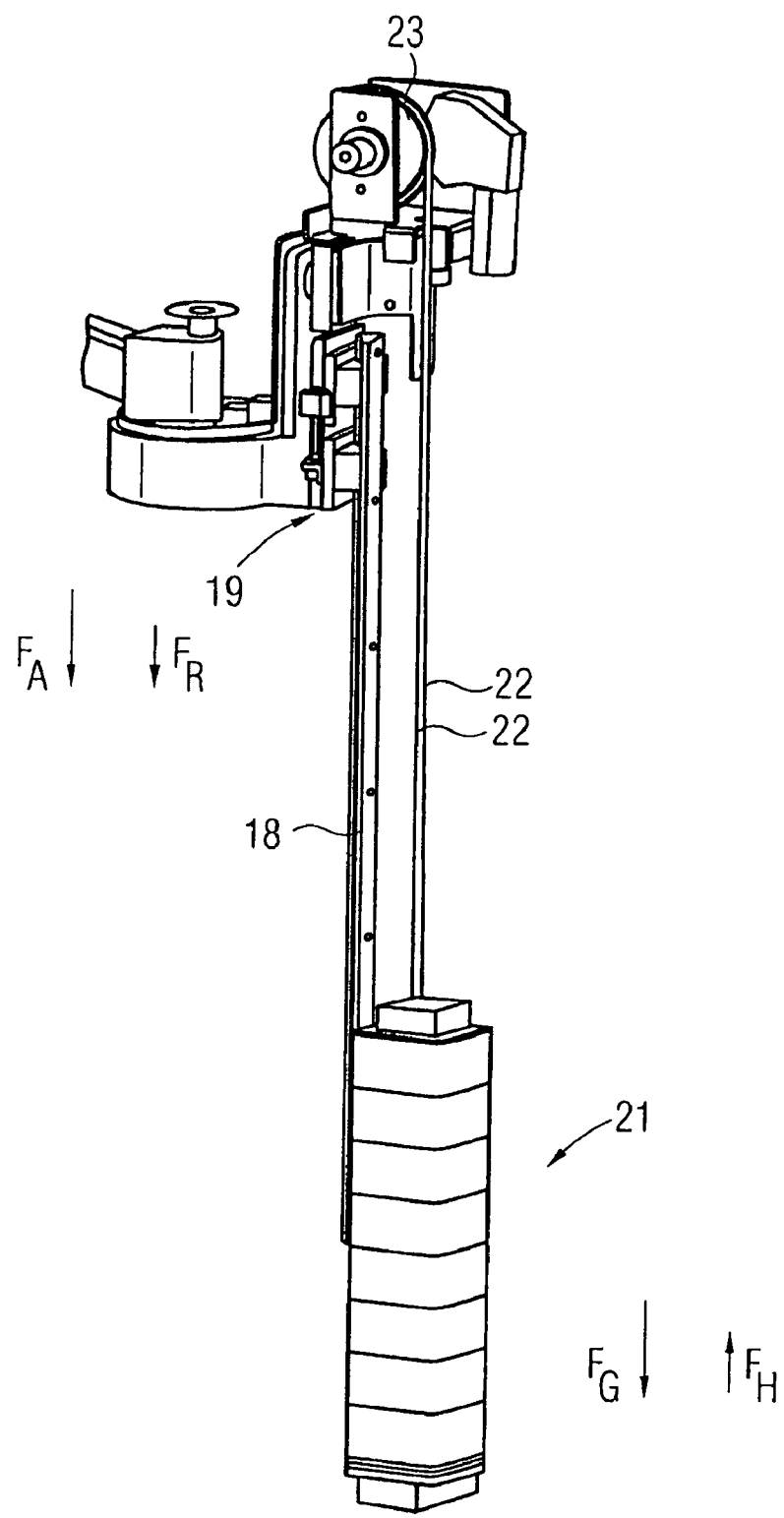
FIG. 3 shows one embodiment of an arm with a linear guide.

FIG. 3 shows a counterweight 21, which is accommodated inside the vertical column 17 and may also include a plurality of parts. The counterweight 21 is connected to the guide carriage 19, and therefore to the arm 6, via two traction devices 22, which are guided via a double traction roller 23. The traction devices 22 may be cables, belts or chains.

A weight of the counterweight 21 is calculated to correspond to a weight of the arm 6 plus a weight of the imaging device 13 so that the arm 6 and the imaging device 13 are counterbalanced in any vertical position (e.g., the imaging device 13 remains in an assumed position without additional vertical locking).

For image capture, the imaging device 13 may be oriented by a user (e.g., a doctor) with respect to an examination subject, and in the case of a mammogram, the imaging device 13 may be placed onto a breast and positioned. The imaging device 13 is detachably mounted to the adapter 11. More specifically, the attachment section 12 is rotationally and swivel mounted via a pivot joint connection on the adapter 11. The pivot joint connection may be locked in any position via a locking device (e.g., by clamping the pivot joint).

The user grasps the imaging device 13 by both bars 32, as shown in FIG. 1, and may position the imaging device 13 relative to a region of interest. The two arms 7, 8 are swiveled into a corresponding position, which is made possible by the first pivot joint 9 and the second pivot joint 10, and at the same time, a vertical position of the imaging device 13 is set accordingly by sliding the imaging device 13 via the linear guide 5.

Figure 4:
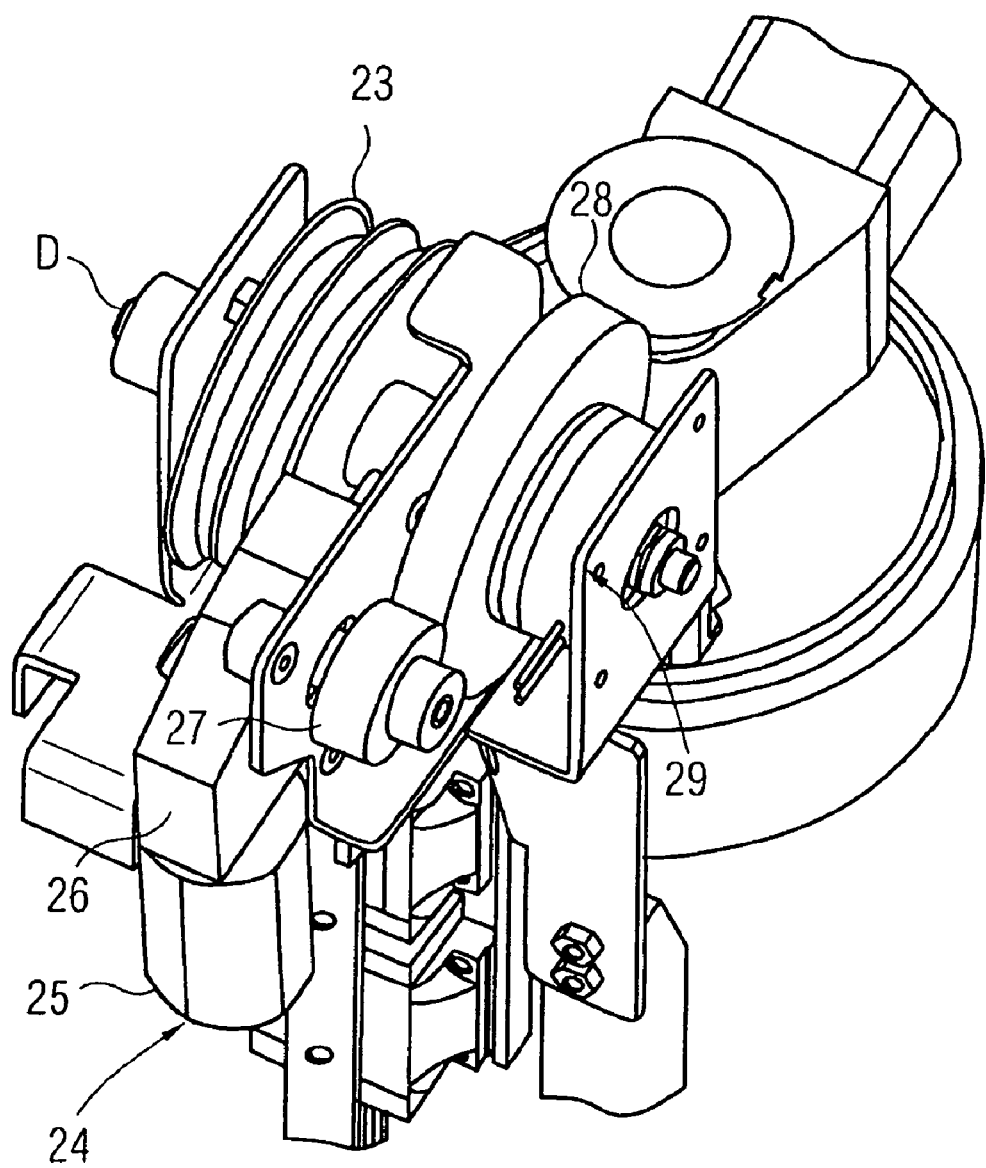
FIG. 4 shows one embodiment of a clutch for a traction roller.
Figure 5:
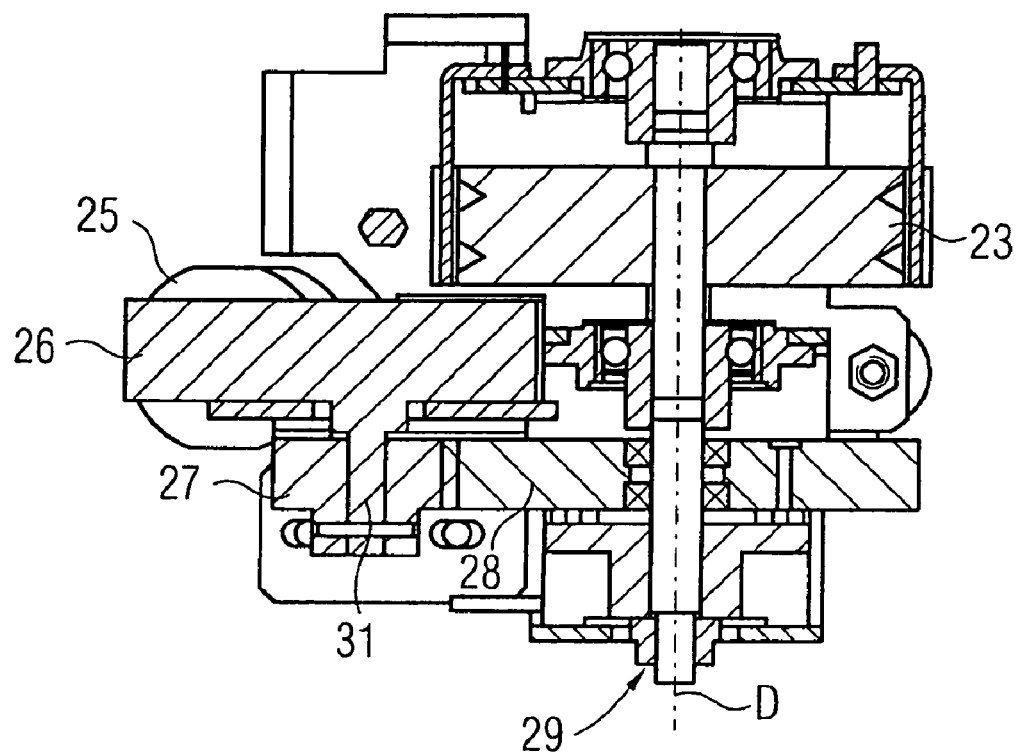
FIG. 5 shows one embodiment of an imaging device.

FIGS. 4 and 5 show a device 24 through which the user may press the imaging device 13 onto the breast with considerable pressure for scanning. The device 24 "lifts" the counterweight 21 after the imaging device 13 has been applied, and therefore, the arm 6 is counter-supported on the patient. The device 24 partially overrides the counterbalancing so that the arm 6 is no longer completely counterbalanced. The arm automatically applies a load via the weight of the arm and presses the imaging device 13 against the breast via an uncounterbalanced weight component.

The device 24 may include a servomotor 25 with a downstream gear 26 via which a first pinion 27 may be driven. The first pinion 27 meshes with a second pinion 28, which, when in an out-of-use position, although ultimately on an axis of rotation D about which the double traction roller 23 rotates, is not coupled to the axis of rotation D in a force-fit manner. The device 24 may include a clutch 29 (e.g., a solenoid operated clutch, which is implemented as a bilaterally acting friction clutch) to establish a force-fit connection between the second pinion 28 and the axis of rotation D. After a force-fit drive connection has been effected via the clutch 29, the motor 25 rotates the first pinion 27, and the axis of rotation D is subjected to a torque via the second pinion 28, which is coupled in a force-fit manner to the axis of rotation D, causing the counterweight 21 to be "lifted." In other words a force acting counter to a weight force of the counterweight 21 is produced. Because of the torque applied to the axis of rotation D, the counterweight 21 is "lifted" (i.e., unloaded), thereby causing a resulting force on the arm 6 to be produced, pressing the arm 6, together with the imaging device 13, onto the region of interest. In FIG. 3, the weight force of the counterweight 21 is represented by $F_G$ and the weight force of the arm 6, including the imaging device 13, is represented by $F_A$. If a force overriding the full counterbalancing is introduced into the traction system via the servomotor 25, this acts as a counter-force $F_H$, counteracting but lower than the weight force $F_G$. The resulting force, which is then provided from the arm 6, is given by $F_R$ in FIG. 3.

After the user has positioned the imaging device 13, and, if necessary, has locked the pivot joint connection on the adapter 11, the user may actuate the device 24 in order to "lower" the arm 6 (i.e., generate the force, $F_R$, with which the arm 6 presses the imaging device 13 with sufficient force onto the region of interest). Each bar 32 may include a separate actuating element 30 via which the device 24 may be controlled to produce the counter-force $F_H$ and to release the counter-force $F_H$ when counterbalancing is to be restored. The user finds the separate actuating elements 30 within reach of where the user grasps to position the imaging device 13, thereby making it easily and conveniently possible to select or turn off automatic loading via the arm 6.

FIG. 5 shows a cross-sectional view of the device 24, and shows the servomotor 25, the downstream gear 26 and the first pinion 27 on a drive shaft 31 of the downstream gear 26 as block diagrams. The first pinion 27 meshes with the second pinion 28, which, although on the axis of rotation D, is not in operative or drive connection with the axis of rotation D. Also shown FIG. 5 is the clutch 29. If the clutch 29 is open and the servomotor 25 is switched on, the first pinion 27 would mesh with the second pinion 28, and the second pinion would rotate. However, because of the absence of a drive connection, no torque is transmitted to the axis of rotation D. Only when the clutch 29 (e.g., the solenoid operated clutch) closes is the second pinion 28 drive-connected to the axis of rotation D via the clutch 29. The torque transmitted via the first pinion 27 to the second pinion 28 may be transferred via the second pinion 28 to the axis of rotation D, which in turn results in rotation of the double traction roller 23.

The clutch 29 may be a bilaterally acting friction clutch. In other words, when the servomotor 25, after closing of the clutch (which is preferably closed immediately by actuating one of the separate actuating elements 30) turns on, the servomotor 25 may transmit up to a maximum torque depending on the design of the clutch 29. The torque determines the magnitude of the opposing force $F_H$ and from the opposing force $F_H$, the resulting weight force $F_R$. When the maximum torque is attained, the clutch 29 slips. In other words, the torque cannot be increased further and the arm 6 presses on the image processing device 13 with maximum possible load.

The clutch 29 also slips in the event of sufficiently high loading from the arm 6. This may be the case when a patient pushes the arm 6 up against the resulting weight force $F_R$ (e.g., if the patient experiences fear or anxiety). In this case the clutch 29 does not lock (e.g., preventing the patient from freeing himself from the situation). The clutch 29 will slip when a sufficiently high torque has developed on the shaft D. This sufficiently high torque is developed by the guide carriage of the vertical guide rail 18 being pushed upward (e.g., a force opposing the resulting force $F_R$ is developed, which is greater than the resulting force). As a result, the counterweight 21 is in turn "loaded." In other words, the counterweight 21 moves downward, and as a result, a torque is applied to the double traction roller 23 in the opposite direction. If this torque is sufficiently large, (e.g., if the counterweight is unloaded to a sufficient extent due to the lifting of the arm) slipping of the clutch 29 again occurs so that the arm 6 can be readily pushed up again, even if the servomotor 25 is still operating.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A stand comprising:
   an arm for holding an object,
   a vertical column, on which the arm is mounted and movable vertically via a vertical guide,
   a counterweight that is supported by the vertical column and interacts with the arm such that the weight of the arm is balanced, and
   a device operable to vary the counterbalancing that interacts with the counterweight such that a resulting weight force acting in the direction of the weight force of the arm is produced,
   wherein the device operable to vary the counterbalancing at least partially overrides the counterbalancing and engages an axis of rotation of a traction roller, via which a traction device runs, connecting the arm to the counterweight.

2. The stand as claimed in claim 1 wherein the device operable to vary the counterbalancing further comprises a servomotor for driving the axis of rotation.

3. The stand as claimed in claim 2, wherein the device operable to vary the counterbalancing comprises a clutch that operatively connects the servomotor to the axis of rotation.

4. The stand as claimed in claim 3, further comprising a first pinion that is operable to be driven by the servomotor, the first pinion meshing with a second pinion via the clutch, to bring the first pinion into rotational connection with the axis of rotation.

5. The stand as claimed in claim 4, wherein the clutch comprises a friction clutch.

6. The stand as claimed in claim 4, wherein the clutch comprises a solenoid operated clutch.

7. The stand as claimed in claim 3, wherein the clutch comprises a friction clutch.

8. The stand as claimed in claim 7, wherein the clutch comprises a solenoid operated clutch.

9. The stand as claimed in claim 7, wherein the clutch is operable to slip both in the event of excessively large loading via the servomotor and in the event of excessively large loading of the axis of rotation via the arm.

10. The stand as claimed in claim 9, wherein the clutch comprises a solenoid operated clutch.

11. The stand as claimed in claim 9, wherein the device operable to vary the counterbalancing is controlled via at least one actuating element located on the arm or on the object.

12. The stand as claimed in claim 3, wherein the clutch comprises a solenoid operated clutch.

13. The stand as claimed in claim 1, wherein the device operable to vary the counterbalancing is controlled via at least one actuating element located on the arm or on the object.

14. The stand as claimed in claim 13, wherein the at least one actuating element is operable to override the counterbalance and reset the counterbalance.

15. The stand as claimed in claim 1, wherein the device operable to vary the counterbalancing is controlled via at least one actuating element located on the arm or on the object.

16. The stand as claimed in claim 1, wherein the object is an imaging device.

17. The stand as claimed in claim 16, wherein the imaging device is an ultrasound transducer.

18. The stand as claimed in claim 1, wherein the stand is a floor stand.

* * * * *